(12) United States Patent
García et al.

(10) Patent No.: US 8,897,536 B2
(45) Date of Patent: Nov. 25, 2014

(54) MOLECULAR BLOCK-MATCHING METHOD FOR GEL IMAGE ANALYSIS

(75) Inventors: Francisco Blanco García, A Coruña (ES); Cristina Ruiz Romero, A Coruña (ES); Julián Alfonso Dorado De La Calle, A Coruña (ES); Alejandro Celestino Pazos Sierra, A Coruña (ES); Ana Belén Porto Pazos, A Coruña (ES); Juan Ramón Rabuñal Dopico, A Coruña (ES); Cristian Robert Munteanu, A Coruña (ES); Ana Maria Freire Veiga, Rabade (ES); Jose Antonio Seoane Fernández, Ferrol (ES); Alvaro Rodriguez Tajes, Villagarcia Arousa (ES); Enrique Fernández Blanco, Vigo (ES); Carlos Fernandez Lozano, Lugo (ES); Javier Pereira Loureiro, A Coruña (ES)

(73) Assignees: Universidade da Coruna. OTRI, a Coruna (ES); Servizo Galego de Saude (Sergas), Santiago de Compostela (ES)

( * ) Notice: Subject to any disclaimer, the term of this patent is extended or adjusted under 35 U.S.C. 154(b) by 382 days.

(21) Appl. No.: 13/454,293

(22) Filed: Apr. 24, 2012

(65) Prior Publication Data
US 2013/0108140 A1    May 2, 2013

Related U.S. Application Data

(60) Provisional application No. 61/478,533, filed on Apr. 24, 2011.

(51) Int. Cl.
*G06K 9/00* (2006.01)
*G01N 27/447* (2006.01)

(52) U.S. Cl.
CPC ...... *G06K 9/00147* (2013.01); *G01N 27/44704* (2013.01)
USPC ........................... 382/133; 382/128; 382/132

(58) Field of Classification Search
None
See application file for complete search history.

(56) References Cited

U.S. PATENT DOCUMENTS

| 5,235,522 | A  * | 8/1993 | Bacus | 702/19 |
| 6,535,624 | B1 * | 3/2003 | Taylor, Jr. | 382/128 |

(Continued)

OTHER PUBLICATIONS

Zeev Smilansky, Automatic registration for images of two dimensional protein gels, Electrophoresis 2001, 22, 1616-1626.*

(Continued)

*Primary Examiner* — Chan Park
*Assistant Examiner* — Iman K Kholdebarin
(74) *Attorney, Agent, or Firm* — Mateo Aboy; Aboy & Associates PC (57) ABSTRACT

A method for analysis of 2-D gel images obtained using electrophoresis. More particularly, a molecular block-matching method for establishing the correspondence between protein spots in a diagnostic-test image and protein spots in a reference image. Individual protein spot matching is performed, thereby removing the need for alignment of the entire reference and test images and permitting automatic labeling of individual protein spots. The method for analysis of 2-D gel images is fully automated, thus making it ideally suited for protein information retrieval systems.

1 Claim, 7 Drawing Sheets

(56) References Cited

U.S. PATENT DOCUMENTS

| | | | |
|---|---|---|---|
| 6,815,189 B1* | 11/2004 | Velasco Alvarez et al. | 435/196 |
| 7,155,050 B1* | 12/2006 | Sloge et al. | 382/133 |
| 2003/0129666 A1* | 7/2003 | Tanaka et al. | 435/7.2 |
| 2004/0110209 A1* | 6/2004 | Yokota et al. | 435/6 |
| 2006/0068452 A1* | 3/2006 | Goldknopf et al. | 435/7.23 |
| 2009/0080725 A1* | 3/2009 | Zbilut et al. | 382/128 |
| 2010/0283785 A1* | 11/2010 | Satulovsky | 345/440 |
| 2011/0142890 A1* | 6/2011 | Alonso Fernandez et al. | 424/401 |
| 2011/0183400 A1* | 7/2011 | de Castro et al. | 435/196 |

OTHER PUBLICATIONS

M Rogers, J Graham and R P Tonge, "Automatic Construction of Statistical Shape Models for Protein Spot Analysis in Electrophoresis Gels", Proceedings of the British Machine Vision Conference, 2003.*

Watanabe, Automated detection and matching of spots in autoradiogram images of two-dimensional electrophoresis for high-speed genome scanning Image Processing, 1997. Proceedings., International Conference on (vol. 3 ) Date of Conference: Oct. 26-29, 1997.*

Zeev Smilansky, Automatic registration for images of two dimensional protein gels, Electrophoresis 2001,22, 1616-1626.*

M Rogers, J Graham and R P Tonge, "Automatic Construction of Statistical Shape Models for Protein Spot Analysis in V Electrophoresis Gels", Proceedings of the British Machine Vision Conference, 2003.*

Garrels, Two dimensional gel electrophoresis and computer analysis of proteins synthesized by clonal cell lines. J. Bio, Chem 1979, 254:7961-7977.*

Watanabe, Automated detection and matching of spots in autoradiogram images of two-dimensional electrophoresis for high-speed genome scanning Image Processing, 1997. Proceedings., International Conference on (vol. 3) Date of Conference: Oct. 26-29, 1997.*

* cited by examiner

| GEL COMPLEXITY | BLOCK SIZE (PIXELS) | SEARCH REGION SIZE (PIXELS) |
|---|---|---|
| LOW | 75 X 75 | 150 X 150 |
| MEDIUM | 75 X 75 | 150 X 150 |
| HIGH | 150 X 150 | 275 X 275 |

FIG.5

| GEL COMPLEXITY | PROTEIN TYPE | n | n CORRECT | n INCORRECT | fc | cn | % CORRECTNESS |
|---|---|---|---|---|---|---|---|
| LOW | DARK | 100 | 100 | 0 | 0 | 0 | 100.00% |
| | FAINT | 96 | 92 | 4 | 2 | 2 | 95.83% |
| | BIG | 63 | 63 | 0 | 0 | 0 | 100.00% |
| | SMALL | 90 | 89 | 1 | 0 | 1 | 98.89% |
| | ISOLATED | 74 | 74 | 0 | 0 | 0 | 100.00% |
| | OVERLAPPING | 81 | 80 | 1 | 1 | 0 | 98.77% |
| | % TOTAL CORRECTNESS: | | | | | | 98.81% |
| MEDIUM | DARK | 72 | 71 | 1 | 1 | 0 | 98.61% |
| | FAINT | 77 | 74 | 3 | 1 | 2 | 96.10% |
| | BIG | 43 | 43 | 0 | 0 | 0 | 100.00% |
| | SMALL | 78 | 77 | 1 | 1 | 0 | 98.72% |
| | ISOLATED | 72 | 71 | 1 | 1 | 0 | 98.61% |
| | OVERLAPPING | 48 | 46 | 2 | 2 | 0 | 95.83% |
| | % TOTAL CORRECTNESS: | | | | | | 97.95% |
| HIGH | DARK | 95 | 84 | 11 | 6 | 5 | 88.42% |
| | FAINT | 37 | 30 | 7 | 4 | 3 | 81.08% |
| | BIG | 68 | 63 | 5 | 4 | 1 | 92.65% |
| | SMALL | 72 | 59 | 13 | 4 | 9 | 81.94% |
| | ISOLATED | 60 | 50 | 10 | 4 | 6 | 83.33% |
| | OVERLAPPING | 78 | 50 | 28 | 22 | 6 | 64.10% |
| | % TOTAL CORRECTNESS: | | | | | | 81.95% |

FIG.6

| ANALYSIS METHOD | LOW GEL COMPLEXITY | | | |
|---|---|---|---|---|
| | n | $n_{CORRECT}$ | $n_{INCORRECT}$ | CORRECT |
| A | 208 | 187 | 21 | 89.9% |
| B | | 201 | 7 | 96.6% |
| C | | 200 | 8 | 96.2% |
| D | | 203 | 5 | 97.6% |
| MOLECULAR BLOCK-MATCHING | | 207 | 1 | 99.5% |

| ANALYSIS METHOD | MEDIUM GEL COMPLEXITY | | | |
|---|---|---|---|---|
| | n | $n_{CORRECT}$ | $n_{INCORRECT}$ | CORRECT |
| A | 158 | 137 | 21 | 86.7% |
| B | | 149 | 9 | 94.3% |
| C | | 150 | 8 | 94.9% |
| D | | 153 | 5 | 96.8% |
| MOLECULAR BLOCK-MATCHING | | 154 | 4 | 97.5% |

| ANALYSIS METHOD | HIGH GEL COMPLEXITY | | | |
|---|---|---|---|---|
| | n | $n_{CORRECT}$ | $n_{INCORRECT}$ | CORRECT |
| A | 55 | - | - | - |
| B | | - | - | - |
| C | | - | - | - |
| D | | - | - | - |
| MOLECULAR BLOCK-MATCHING | | 47 | 8 | 85.5% |

FIG.7

MOLECULAR BLOCK-MATCHING METHOD FOR GEL IMAGE ANALYSIS

CROSS-REFERENCE TO RELATED APPLICATIONS

This application claims the benefit of U.S. Provisional Application No. 61/478,533 filed on Apr. 24, 2011 by the present inventors, which is incorporated herein by reference.

TECHNICAL FIELD

Disclosed embodiments relate to the analysis of gel images obtained using electrophoresis. Specifically, they relate to computational methods for establishing the correspondence between proteins of different 2-D gels.

BACKGROUND

The images of 2-D gels resulting from electrophoresis are a powerful biomedical diagnosis mechanism. The proteins of tissue, blood, cell, etc, are separated and analyzed by placing the proteins on a polyacrylamide gel and applying an electrical potential difference across it. The separation follows a bidimensional pattern according to the molecular weight and isoelectrical point of the proteins.

When analyzing gel images, a reference image that represents the distribution of a sample of proteins in normal conditions (normal health status) is utilized. The protein spots shown in reference images are labeled and have a known spatial location. Diagnostic test images are then generated, in which the identification and spatial location of the protein spots is unknown. Usually, a comparison between a test image and the reference image is performed in order to establish the correspondence between protein spots in both images. For each pair of corresponding protein spots, one protein spot in each image represents the same protein. For each pair of corresponding protein spots, the difference between the characteristics of each of protein spot infers information about changes to a particular protein. Extracting this information for a relevant subset of proteins can be used to diagnose a medical condition or to test for the presence of a drug, etc.

Although gels images are increasingly used in the biomedical field, the analysis of such images is becoming more difficult due to the variability between different electrophoresis processes. Consequently, test images with a complex correspondence to reference images may be obtained. The location, shape, size, and intensity of any given protein spot may vary between images or the protein may not appear in one of the images, such that correspondence between proteins in the test and reference images is difficult or impossible to establish. Since each gel may contain thousands of proteins, computational techniques are essential for efficient gel image analysis.

SUMMARY

Disclosed embodiments of the method for gel image analysis implemented in a medical system with one or more processors include: (a) receiving an indication of the location of a first protein spot on a first gel image; and (b) locating a second protein spot on a second gel image using a molecular block-matching method, the second protein spot represents the same protein as the first protein spot.

Disclosed embodiments of the molecular-block-matching method for gel image analysis implemented in a medical system with one or more processors include: (a) centering a first block on a first gel image at the location of a first protein spot; (b) centering a second block on a second gel image at an initial location corresponding to the location of the first protein spot on the first gel image; (c) shifting the second block by increments up to a maximum displacement from the initial location; (d) comparing the images within the first and second blocks prior to each incremental shift of the second block, in order to determine the closest matching second block to the first block; and (e) assigning the center location of the closest matching second block to a second protein spot on the second gel image.

BRIEF DESCRIPTION OF THE DRAWINGS

Disclosed embodiments are illustrated by way of example, and not by way of limitation, in the figures of the accompanying drawings.

DETAILED DESCRIPTION

Certain specific details are set forth in the following description and figures to provide a thorough understanding of various embodiments disclosed. Certain well-known details often associated with computing and software technology are not set forth in the following disclosure to avoid unnecessarily obscuring the various disclosed embodiments. Further, those of ordinary skill in the relevant art will understand that they can practice other embodiments without one or more of the details described below. Aspects of the disclosed embodiments may be implemented in the general context of computer-executable instructions, such as program modules, being executed by a computer, computer server, or device containing a processor. Generally, program modules include routines, programs, objects, components, data structures, etc. that perform particular tasks or implement particular abstract data types. Aspects of the disclosed embodiments may also be practiced in distributed computing environments where tasks are performed by remote processing devices that are linked through a communications network. In a distributed computing environment, program modules may be located in both local and remote storage media including memory storage devices. Those skilled in the art will appreciate that, given the description of the modules comprising the disclosed embodiments provided in this specification, it is a routine matter to provide working systems which will work on a variety of known and commonly available technologies capable of incorporating the features described herein.

A. Method for Gel Image Analysis

Analysis of gels images broadly comprises the following steps: (a) identifying protein spot centers in reference and test images by their approximate coordinates, (b) establishing the correspondence between proteins spots in test and reference images, (c) quantifying and analyzing the differing characteristics of the corresponding protein spots in the test and reference images in order to form an expression profile used for diagnosis.

According to one embodiment, and without limitation, the method for gel image analysis disclosed herein is primarily directed toward establishing correspondence between protein spots in reference and test gel images. The input into this method includes the test and reference gel image files, and the approximate coordinates of protein spots of interest within the reference image. The approximate coordinates of the protein spots in the reference image can be generated by techniques such as described in Langella et al., "A method based on bead flows for spot detection on 2-D gel images", *Proteomics*, 8:4914-4918 (2008), or can be generated by a spot picking robot, such as GelPix®. The output of the method for gel image analysis includes the magnitude and direction of displacement of the corresponding protein spots in the test and reference images.

Figure 1:
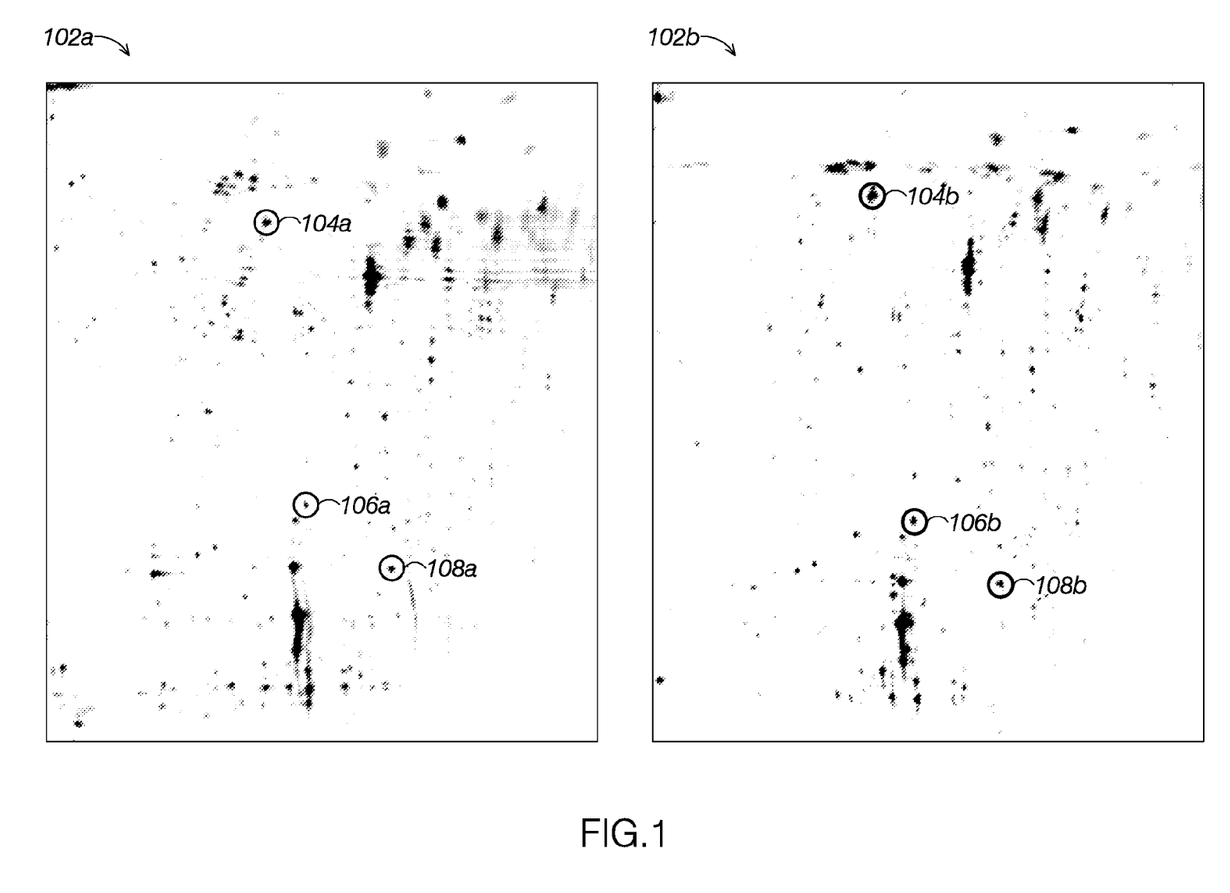
FIG. 1 illustrates a typical pair of 2D electrophoretic gel images created from the same sample.

A typical pair of 2-D electrophoretic gel images 102a-102b, created using the same proteomic sample, is shown in FIG. 1. Each dark spot represents one of the several protein types present in the sample and its spot size indicates the amount of protein present. However, the experimental setting and materials used to create proteomic gels result in variations between corresponding proteins in different gels, such as between the corresponding proteins pairs represented by 104a-104b, 106a-106b, and 108a-108b in FIG. 1. Several computer vision optical flow estimation techniques have been studied with the aim of finding a solution for the protein spot matching task. Particularly, the technique must be suitable for measuring displacements due to nonlinear movements with a high degree of deformation, since these are normal characteristics of viscous fluids (polyacrylamide gels). Regional fitting (block-matching) techniques have been chosen as the starting point for developing a method suitable for gel image analysis.

However, standard block-matching techniques are best suited for analysis of image sequences (with few changes from one image frame to the next one), whilst gel images are independent (with nonlinear movements and a high degree of deformation). Therefore, a new method for gel image analysis has been developed, which uses the molecular block-matching method disclosed herein.

Figure 2:
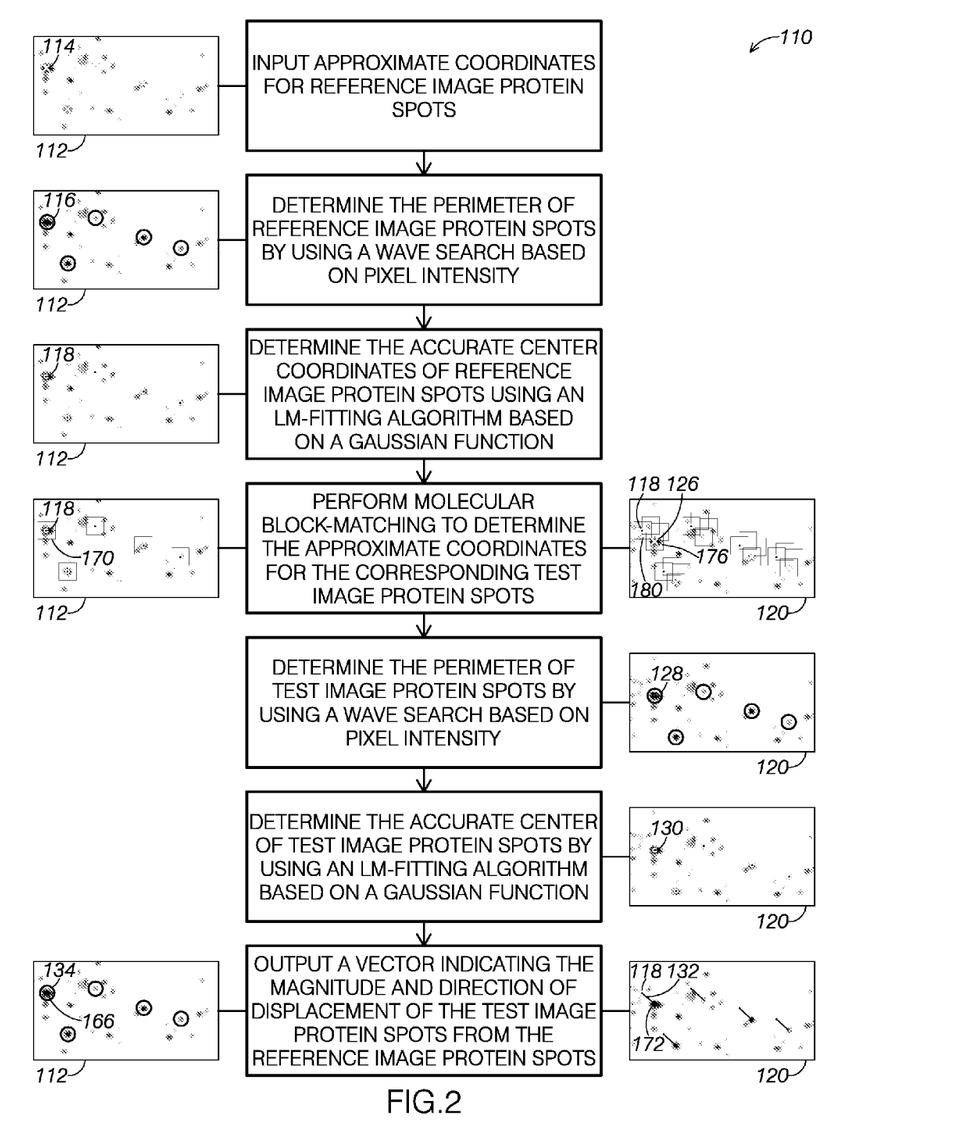
FIG. 2 illustrates a block diagram representing an embodiment of the method for gel image analysis.

According to one embodiment, and without limitation, the method 110 for gel image analysis, implemented in a digital computer with one or more processors, is shown in FIG. 2. The method 110 for gel image analysis receives the approximate coordinates 114 of each protein spot of interest on a reference gel image 112. At the approximate coordinates 114 of each protein spot, a minimum radius is selected and this radius value is increased until the edge of the protein spot is detected (indicated by a pixel intensity value up to a certain grey threshold). For each protein spot, the perimeter 116 of the circle with final radius value centered at the approximate coordinates of the protein spot is established, and the accurate center of the protein spot is assumed to lie within the established perimeter 116.

For each protein spot, once a perimeter 116 has been established, the accurate center is located using a Levenberg-Marquardt fitting algorithm to model pixel intensity within the area established by the perimeter 116. An inverted bidimensional Gaussian function was chosen as the fitting function for the proteins' grey level, since it is a continuous-function and adequately describes the distribution of grey level within each protein spot. The accurate center coordinates 118 of each protein spot is determined to be the minimum (lowest grey level) in the inverted Gaussian curve, which undergoes a rotation geometrical transformation to model all possible 2-D orientations of the protein spot.

Figure 4:
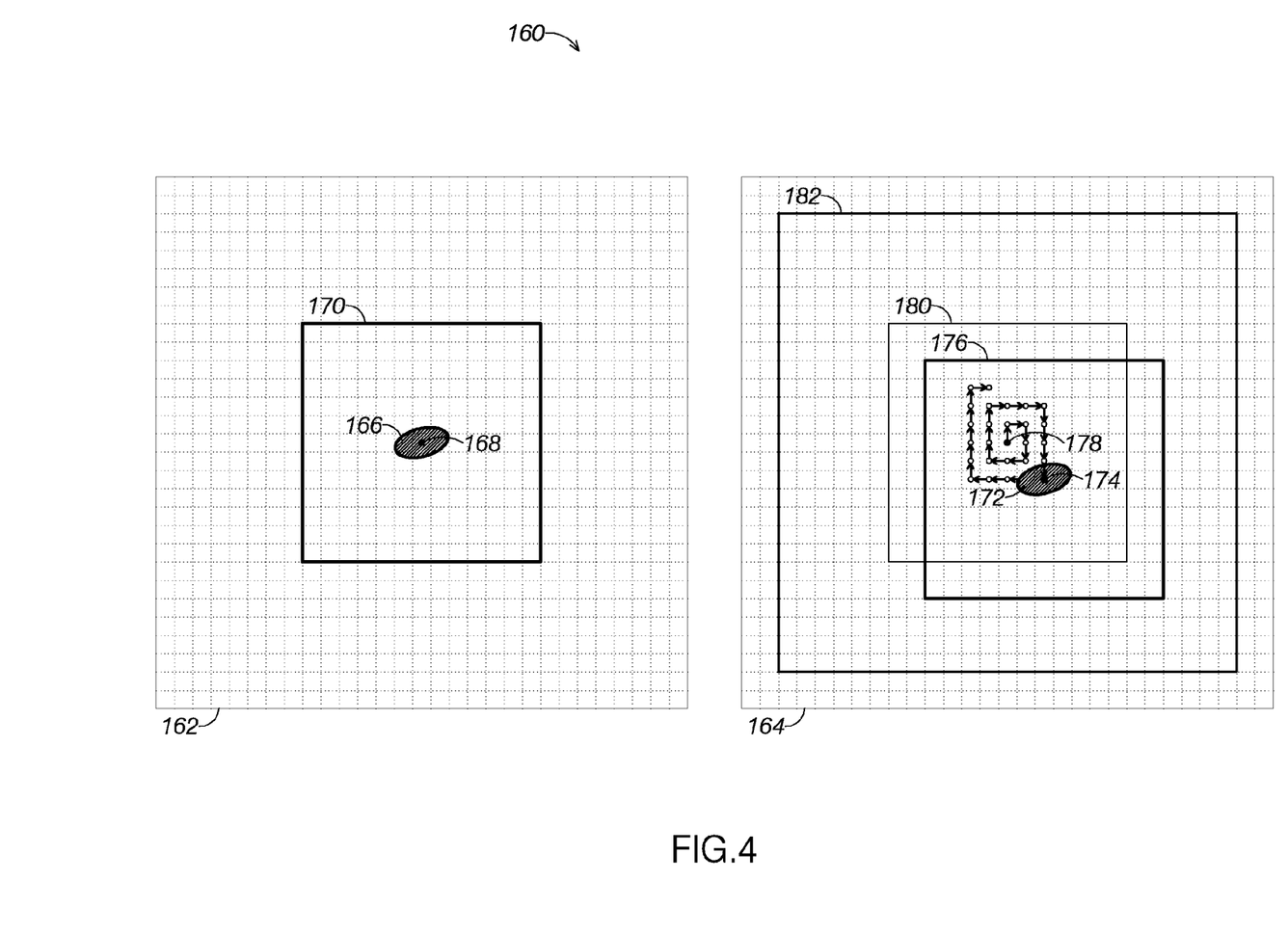
FIG. 4 illustrates a diagram representing an embodiment of the molecular block-matching method for gel image analysis.

Once the center coordinates 118 of all protein spots of interest in the reference image 112 have been established, the embodiment of the molecular block-matching method 160 for gel image analysis, shown in FIG. 4, is applied in order to identifying the approximate coordinates 126 of the corresponding protein spots in the test image 120. The molecular block-matching method 160 for gel image analysis is described in Section B below.

At the approximate coordinates 126 of each corresponding protein spot in the test image 120, a minimum radius is selected and this radius value is increased until the edge of the protein spot is detected (indicated by a pixel intensity value up to a certain grey threshold). For each protein spot, the perimeter 128 of the circle with final radius value centered at the approximate coordinates of the protein spot is established 120, and the accurate center 130 of the protein spot is assumed to lie within the established perimeter 128.

For each protein spot, once a perimeter 128 has been established, the accurate center 130 is located using a Levenberg-Marquardt fitting algorithm to model pixel intensity within the area established by the perimeter 128. An inverted bidimensional Gaussian function was chosen as the fitting function for the proteins' grey level, since it is a continuous-function and adequately describes the distribution of grey level within each protein spot. The accurate center 130 of each protein spot is determined to be the minimum (lowest grey level) in the inverted Gaussian curve, which undergoes a rotation geometrical transformation to model all possible 2-D orientations of the protein spot.

Figure 3:
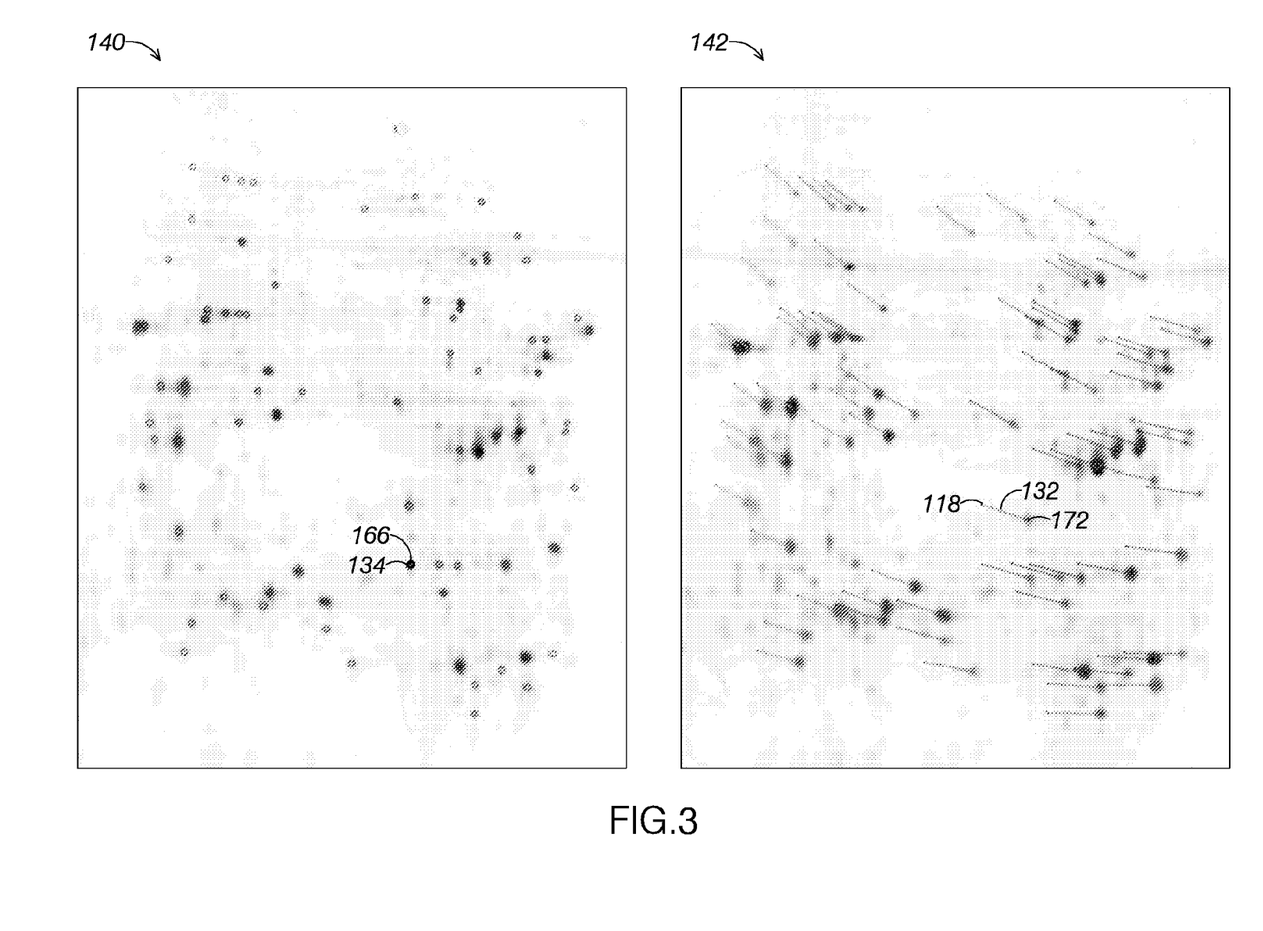
FIG. 3 illustrates a typical pair of output 2D electrophoretic gel images created by the embodiment of the method for gel image analysis shown in FIG. 2.

This embodiment of the method for gel image analysis returns a reference image 112 in which all proteins of interest 166 are marked 134, and a test image 120 in which the identified proteins of interest 172 appear with a vector 132 that indicates not only the direction, but also the magnitude of their displacement in relation to their corresponding protein spots 166 in the reference image 112. Full size representations of the reference 140 and test 142 output images are shown in FIG. 3.

Alternate embodiments of the method 110 for gel image analysis receive other locational data for the proteins of interest instead of approximate coordinates, and extrapolates that locational information to identify the approximate coordinates.

Alternate embodiments of the method 110 for gel image analysis return only the test image 142, output a visual representation of the displacement information in an alternative format, or output electronic data, or any combination of the foregoing.

B. Molecular Block-Matching Method for Gel Image Analysis

According to one embodiment, and without limitation, the molecular block-matching method 160 for gel image analysis, implemented in a digital computer with one or more processors, is shown in FIG. 4 (not to scale). The molecular block-matching method 160 for gel image analysis centers a reference block 170 at the location 168 of the protein spot 166 on the reference image 162. The reference block size is specified in the table of FIG. 5. An initial search block 180 (of same size as the reference block) is defined on the test image 164 and is centered on an initial location 178 of the test image 164 corresponding to the location 168 of the protein spot 166 in the reference image 162.

A spiral search strategy is implemented, as shown in FIG. 4, starting from the initial position 178 of the center of the initial search block 180, with successive hops of one pixel. In this way, the entire search region 182 is explored. The search region size, as specified in the table of FIG. 5, limits the displacement of the shifted search block 176 from its initial center location 178. Prior to each hop the current search block is compared to the reference block 170 using Pearson's correlation as a block comparison criterion. In this way, the closest matching search block 176, which generates the best value for Pearson's correlation coefficient, is identified. The center coordinates 174 of the closest matching search block 176 are assumed to be the approximate center coordinates 174 of the corresponding protein spot 172 in the test image 164 to the protein spot 166 in the reference image 162.

Alternate embodiments of the molecular block-matching method 160 for gel image analysis use different parameters for: block shape, block size, search region shape, search region size, and/or search hop step; and the search strategy can be implemented with any search pattern that explores the search region.

C. Testing & Results of Method for Gel Image Analysis

In order to understand the results, it is necessary to define several terms:

Success: occurs when the protein spot center calculated by the method for gel image analysis falls within the perimeter of the corresponding protein spot to the one in the reference image.

Failure: occurs when the protein spot center calculated by the method for gel image analysis falls outside of the perimeter of corresponding protein spot to the one in the reference image. Furthermore, failures are divided into false matchings (the protein spot center calculated falls within the perimeter of a non-corresponding protein spot) and negative matchings (the protein spot center calculated falls outside of all protein spots). Both success and failure determinations are based on manual analysis of the spatial location and characteristics of the protein spots, and the evaluation was subject an expert's review.

Protein spot: any region of a gel image with a grey level less than 150 and darker than its surroundings.

Intensity: grey level of pixels within protein spots (i.e. degree of differentiation from the image background). Intensity can be highly expressed (dark): region of protein spot with grey level less than 100. Intensity can be poorly expressed (light): region of protein spot with grey level in range 100-150.

Size: protein spot diameter. Size can be big: diameter greater than 15 pixels. Size can be small: diameter less than 13 pixels.

Proximity: proximity to other proteins. Proximity can be isolated: entire perimeter of protein spot is clearly defined and there is no overlapping with other dark regions. Proximity can be overlapping: perimeter of protein spot partially overlaps other dark regions.

C1. Determination of Optimal Block Size and Search Region Size:

The reference and test images are 2-D gel images created from different tissues under different experimental conditions. The images were grouped into: (a) five pairs of images in which the protein spots could be visually correlated with no difficulty (low complexity), (b) five pairs of images in which most of the protein spots could be visually correlated, but correlation is harder to establish (medium complexity), and (c) five pairs of images in which most of the proteins could not be visually correlated (high complexity).

Figure 5:
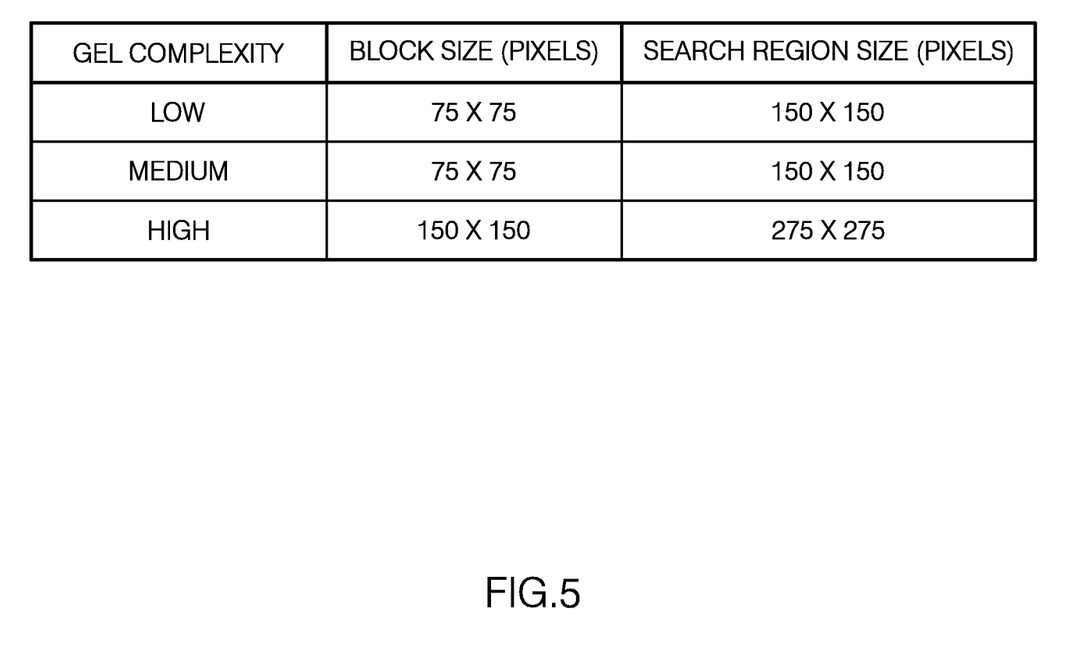
FIG. 5 illustrates a table of block size parameters and search region size parameters used by the embodiment of the method for gel image analysis shown in FIG. 2.

The optimal block size and search region size for low, medium, and high complexity gel images, determined through running multiple iterations of the method for gel image analysis on all image pairs in each complexity group, are shown in the table of FIG. 5.

C2. Determination of the Success Rate of the Method for Gel Image Analysis for Different Types of Gel Images:

The reference and test images are 2-D gel images created from different tissues under different experimental conditions. The images were grouped into: (a) five pairs of images in which the protein spots could be visually correlated with no difficulty (low complexity), (b) five pairs of images in which most of the protein spots could be visually correlated, but correlation is harder to establish (medium complexity), and (c) five pairs of images in which most of the proteins could not be visually correlated (high complexity).

Figure 6:
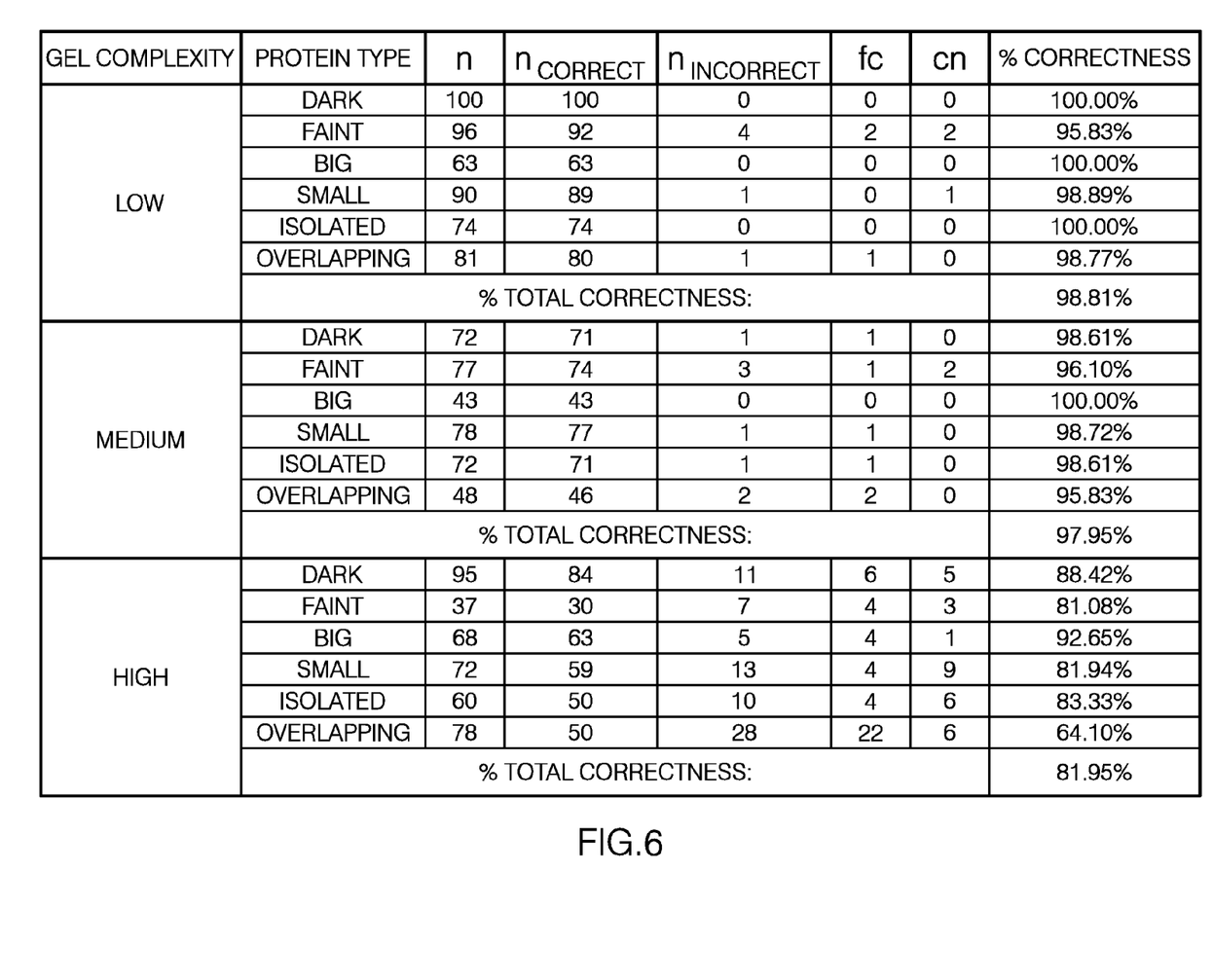
FIG. 6 illustrates a table of success rates for low, medium, and high complexity gel images for the embodiment of the method for gel image analysis shown in FIG. 2.

The success rates for the method for gel image analysis for different protein types in low, medium, and high complexity gel images are shown in the table of FIG. 6. For each complexity level, the total number (n) of each protein type selected for analysis is presented. Since each protein spot can exhibit more than one type of characteristic (e.g. dark and overlapping), some of protein spots were included in multiple categories. The detection success and failure categories are as follows: correct ($n_{correct}$), incorrect ($n_{incorrect}$), false matching (fc), and negative matching (nc), and percent of correct detection.

Figure 7:
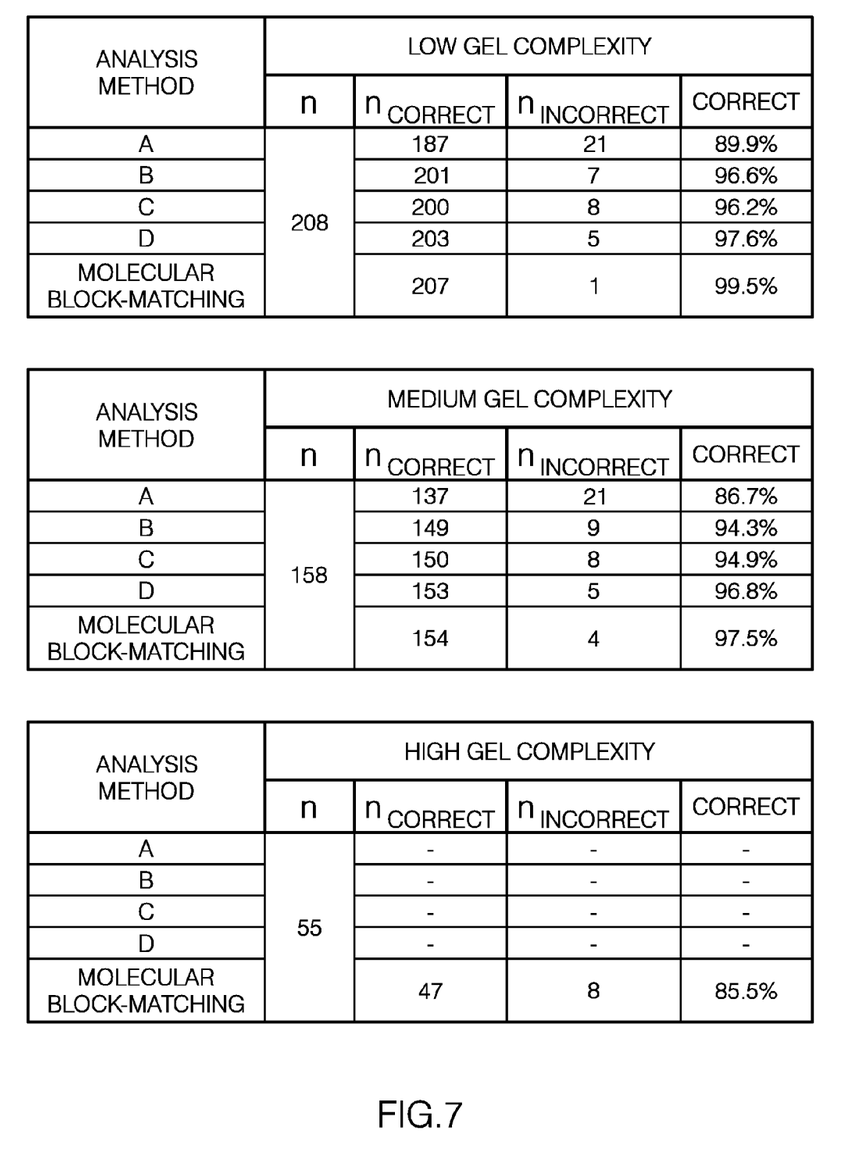
FIG. 7 illustrates a table of success rates for the embodiment of the method for gel image analysis shown in FIG. 2 and success rates for four existing methods for gel image analysis.

C3. Determination of Success Rate of the Method for Gel Image Analysis of the Present Disclosure Compared to Existing Methods for Gel Analysis In order to check the comparative success of the method for gel image analysis of the present disclosure, tests equivalent to those described in two published papers were conducted. Analysis methods A and B, shown in the table of FIG. 7, are described in Rohr et al., "Elastic registration of electrophoresis images using intensity information and point landmarks", Pattern Recognition, 37: 1035-1048 (2004). Analysis methods C and D, shown in the table of FIG. 7, are described in Worz et al., "Geometric alignment of 2D gel electrophoresis images using physics-based elastic registration", *5th IEEE International Symposium on Biomedical Imaging: From Nano to Macro* (2008). Methods A and C utilize an intensity-based approach to gel image analysis, and methods B and D utilize a hybrid landmark and intensity approach. The published methods A-D all attempt to determine corresponding proteins by alignment of the entire test and reference images.

These published methods for gel image analysis were chosen because their published test results are based on 2-D gel images produced by the same laboratory as the source images of the present disclosure (Royal Society/Wolfson MIC Laboratory, Department of Computing, Imperial College of Science, Technology and Medicine, London). In the methods A-D, 208 proteins from low complexity images were analyzed and 158 proteins from medium complexity images were analyzed, but no protein information was published for high complexity images. In order to achieve comparable test results, the same images pairs used in the methods A-D were used by the method for gel image analysis of the present disclosure. In addition, the method for gel image analysis of the present disclosure selected all visually identifiable proteins (55) from the high complexity image pairs.

Since the specific proteins analyzed are not disclosed in the published papers for methods A-D, the method for gel image analysis of the present disclosure analyzed 208 randomly selected proteins (at most 2.4% of the proteins vary from those selected in the published methods A-D) from low complexity images, and analyzed 158 randomly selected proteins (at most 1.27% of the molecules vary from published methods A-D) from medium complexity images. Since these variation rates are minimal, the results can be considered comparable.

The published success rates for methods A-D and the success rates for the method for gel image analysis of the present disclosure, for low, medium, and high complexity gel images, are shown in the table of FIG. 7. For each complexity level, the total number (n) of each protein type selected for analysis is presented. The detection success and failure categories are as follows: correct ($n_{correct}$), incorrect ($n_{incorrect}$), and percent of correct detection.

The success rates for analysis of real biomedical images, obtained by the method for gel image analysis of the present disclosure, were higher than the success rates achieved by existing methods for gel image analysis using the same biomedical images.

D. Conclusions

The method for gel image analysis of the present disclosure, using molecular block-matching, performs individual protein spot matching and thus removes the need for alignment of the entire reference and test images. Consequently, protein spot matching can be performed over a subset of proteins because often only some proteins are important for establishing a medical diagnosis. Furthermore, since individual protein spots are matched, the assignment of protein labels to individual protein spots is readily implemented, thereby avoiding the need for manual labeling. In addition, the method for gel image analysis of the present disclosure is fully automated; thus making it ideally suited for protein information retrieval systems.

While particular embodiments have been described, it is understood that, after learning the teachings contained in this disclosure, modifications and generalizations will be apparent to those skilled in the art without departing from the spirit of the disclosed embodiments. It is noted that the foregoing embodiments and examples have been provided merely for the purpose of explanation and are in no way to be construed as limiting. While the method has been described with reference to various embodiments, it is understood that the words used herein are words of description and illustration, rather than words of limitation. Further, although the method has been described herein with reference to particular means, materials and embodiments, the actual embodiments are not intended to be limited to the particulars disclosed herein; rather, the method extends to all functionally equivalent structures, methods and uses, such as are within the scope of the appended claims. Those skilled in the art, having the benefit of the teachings of this specification, may effect numerous modifications thereto and changes may be made without departing from the scope and spirit of the disclosed embodiments in its aspects.

The invention claimed is:

1. A method for gel image analysis implemented in a medical system with one or more processors, said method comprising:
   (a) receiving the approximate coordinates of a first protein spot on a first gel image;
   (b) identifying the perimeter of said first protein spot using a wave search based on the pixel-intensity of the area surrounding said approximate coordinates;
   (c) identifying the center coordinates of said first protein spot using a Levenberg-Marquardt fitting algorithm to model pixel intensity within said perimeter of said first protein spot, said Levenberg-Marquardt fitting algorithm based on a Gaussian function;
   (d) locating a second protein spot on a second gel image using a molecular block-matching method, said second protein spot represents the same protein as said first protein spot, and said molecular block-matching method comprises:
      i. centering a first block on said first gel image at the center coordinates of said first protein spot,
      ii. centering a second block on said second gel image at an initial location corresponding to the location of said first protein spot on said first gel image,
      iii. shifting said second block in single pixel increments in a widening spiral around said initial location up to a maximum displacement from said initial location,
      iv. comparing the images within said first and second blocks prior to each incremental shift of said second block using Pearson's correlation as a block comparison criterion, in order to determine the closest matching second block to said first block, and
      v. assigning the center location of said closest matching second block as the approximate coordinates of said second protein spot;
   (e) identifying the perimeter of said second protein spot using a wave search based on the pixel-intensity of the area surrounding said approximate coordinates of said second protein spot; and
   (f) identifying the center coordinates of said second protein spot using a Levenberg-Marquardt fitting algorithm to model pixel intensity within said perimeter of said second protein spot, said Levenberg-Marquardt fitting algorithm based on a Gaussian function,
   whereby the magnitude and direction of displacement of said second protein spot relative to said first protein spot can be ascertained.

* * * * *

UNITED STATES PATENT AND TRADEMARK OFFICE
CERTIFICATE OF CORRECTION

PATENT NO. : 8,897,536 B2
APPLICATION NO. : 13/454293
DATED : November 25, 2014
INVENTOR(S) : Alejandro Celestino Pazos Sierra et al.

It is certified that error appears in the above-identified patent and that said Letters Patent is hereby corrected as shown below:

On the title page, item (75), line 1, incorrect order of inventorship. The correct inventorship order should be:
Alejandro Celestino Pazos Sierra, A Coruña (ES)
Julián Alfonso Dorado de la Calle, A Coruña (ES)
Francisco Blanco García, A Coruña (ES)
Javier Pereira Loureiro, A Coruña (ES)
Juan Ramón Rabuñal Dopico, A Coruña (ES)
Cristina Ruiz Romero, A Coruña (ES)
José Antonio Seoane Fernández, A Coruña (ES)
Ana María Freire Veiga, A Coruña (ES)
Enrique Fernández Blanco, A Coruña (ES)
Álvaro Rodríguez Tajes, A Coruña (ES)
Carlos Fernández Lozano, A Coruña (ES)
Ana Belén Porto Pazos, A Coruña (ES)
Cristian Robert Munteanu, A Coruña (ES)

Signed and Sealed this
Twenty-fourth Day of March, 2015

Michelle K. Lee
*Director of the United States Patent and Trademark Office*

UNITED STATES PATENT AND TRADEMARK OFFICE
CERTIFICATE OF CORRECTION

PATENT NO. : 8,897,536 B2
APPLICATION NO. : 13/454293
DATED : November 25, 2014
INVENTOR(S) : Alejandro Celestino Pazos Sierra et al.

Page 1 of 1

It is certified that error appears in the above-identified patent and that said Letters Patent is hereby corrected as shown below:

On the title page, item (12), "Garcia et al." should read -- Pazos Sierra et al. --.

On the title page, item (75), line 1, incorrect order of inventorship. The correct inventorship order should be:
Alejandro Celestino Pazos Sierra, A Coruña (ES)
Julián Alfonso Dorado de la Calle, A Coruña (ES)
Francisco Blanco García, A Coruña (ES)
Javier Pereira Loureiro, A Coruña (ES)
Juan Ramón Rabuñal Dopico, A Coruña (ES)
Cristina Ruiz Romero, A Coruña (ES)
José Antonio Seoane Fernández, A Coruña (ES)
Ana María Freire Veiga, A Coruña (ES)
Enrique Fernández Blanco, A Coruña (ES)
Álvaro Rodríguez Tajes, A Coruña (ES)
Carlos Fernández Lozano, A Coruña (ES)
Ana Belén Porto Pazos, A Coruña (ES)
Cristian Robert Munteanu, A Coruña (ES)

This certificate supersedes the Certificate of Correction issued March 24, 2015.

Signed and Sealed this
Twenty-first Day of April, 2015

Michelle K. Lee
*Director of the United States Patent and Trademark Office*